United States Patent
Kohno et al.

(10) Patent No.: US 7,186,425 B2
(45) Date of Patent: Mar. 6, 2007

(54) COMPOSITION FOR DIMINISHING NEUTRAL FAT IN BLOOD

(75) Inventors: Mitsutaka Kohno, Tsukuba-gun (JP); Motohiko Hirotsuka, Tsukuba-gun (JP); Toshiaki Aoyama, Osaka (JP); Kiyoharu Takamatsu, Osaka (JP); Yukio Hashimoto, Osaka (JP); Makoto Kito, Kyoto (JP)

(73) Assignee: Fuji Oil Company, Ltd., Osaka (JP)

( * ) Notice: Subject to any disclaimer, the term of this patent is extended or adjusted under 35 U.S.C. 154(b) by 276 days.

(21) Appl. No.: 10/381,700

(22) PCT Filed: Sep. 28, 2001

(86) PCT No.: PCT/JP01/08603

§ 371 (c)(1),
(2), (4) Date: Mar. 27, 2003

(87) PCT Pub. No.: WO02/26243

PCT Pub. Date: Apr. 4, 2002

(65) Prior Publication Data

US 2004/0014640 A1   Jan. 22, 2004

(30) Foreign Application Priority Data

Sep. 29, 2000   (JP) ............ 2000-300603

(51) Int. Cl.
*A61K 36/00* (2006.01)
(52) U.S. Cl. .................................... 424/757
(58) Field of Classification Search ........ 424/757
See application file for complete search history.

(56) References Cited

U.S. PATENT DOCUMENTS

| | | | | |
|---|---|---|---|---|
| 3,736,147 A * | 5/1973 | Iacobucci et al. | ........... | 530/377 |
| 4,072,670 A * | 2/1978 | Goodnight et al. | ......... | 530/378 |
| 4,370,267 A * | 1/1983 | Lehnhardt et al. | ......... | 530/378 |
| 4,697,004 A * | 9/1987 | Puski et al. | .................. | 530/378 |
| 4,771,126 A * | 9/1988 | Hirotsuka et al. | .......... | 530/378 |
| 5,248,765 A * | 9/1993 | Mazer et al. | ................. | 530/372 |
| 5,270,450 A * | 12/1993 | Westfall et al. | ............. | 530/378 |
| 5,659,015 A * | 8/1997 | Colon et al. | ................. | 530/351 |
| 6,171,640 B1 * | 1/2001 | Bringe | ....................... | 426/656 |
| 6,313,273 B1 * | 11/2001 | Thomas et al. | ............. | 530/378 |
| 6,638,562 B1 | 10/2003 | Saitoh et al. | | |

FOREIGN PATENT DOCUMENTS

| | | |
|---|---|---|
| EP | 0380343 | 8/1990 |
| EP | 0 922 395 | 6/1999 |
| EP | 1 174 516 | 1/2002 |
| JP | 8-173052 | 7/1996 |
| JP | 9-23822 | 1/1997 |
| JP | 10-203994 | 8/1998 |
| JP | 2000-204369 | 7/2000 |

OTHER PUBLICATIONS

Cai et al.; "Processing Effect on Soybean Storage Proteins and Their Relationship with Tofu Quality," J. Agric. Food Chem.; 47 (2), 720-727, 1999; abstract only (1 pages).*
Ji et al.; "Tofu Yield adn Textural Properties from Three Soybean Cultivars as Affected by Ratios of 7S and 11S Protein," Journal of Food Science; vol. 64, p. 763; Sep. 1999; abstract only (2 pages).*
Takuo Okita et al., "Effects of Dietary Soybean Globulins on Plasma and Liver Lipids and on Fecal Excretion of Neutral Sterols in Rats", J. Nutr. Sci. Vitaminol. vol. 27, No. 4, pp. 379-388, 1981.
M.A. Ritter, et al., "In vitro Digestibility Phytate-reduced and Phenolics-reduced Soy Protein Isolates", J. Food. Sci., vol. 52, No. 2, pp. 325-327, 1987.
M. R. Lovati et al., "Low Density Lipoprotein Receptor Activity Is Modulated by Soybean Globulins in Cell Culture", Journal of Nutrition, Wistar Institute of Anatomy and Biology, vol. 122, pp. 1971-1978, May 1992.
Ruth L. Henn et al., "Biochemical Characterization and Enzymatic Hydrolysis of Different Commercial Soybean Protein Isolates", Journal of Agriculture and Food Chemistry, vol. 46, pp. 3009-3015, 1998.
Liu Guozhi & Sun Ming, "Soy Protein: Function, Nutrition and Application", Oct. 1995, No. 5.

* cited by examiner

*Primary Examiner*—Anne Marie Grunberg
*Assistant Examiner*—S. B. McCormick-Ewoldt
(74) *Attorney, Agent, or Firm*—Wenderoth, Lind & Ponack, LLP

(57) ABSTRACT

The present invention provides a neutral fat reducing composition which reduces a blood neutral fat safely and efficiently, and whose active ingredient is a soybean protein containing 50% or more of a 7S globulin fractionated from a soybean protein and 0.2% or less of phytate based on the proteins. Its effect is further enhanced by removing a oil-body-associated protein and reducing a chloroform methanol-extractable oil fraction.

6 Claims, No Drawings

COMPOSITION FOR DIMINISHING NEUTRAL FAT IN BLOOD

FIELD OF THE INVENTION

The present invention relates to a blood neutral fat reducing composition.

PRIOR ART

Among vegetable proteins, a soybean protein not only has an excellent nutritional property but also was found recently to have various physiological efficacies and became an attractive food material as a physiologically-functional agent.

A blood neutral fat reducing effect of a soybean protein has already been established based on a body fat-reducing effect of the soybean protein, and its mechanism was reported by Iritani, et al., (J. Nutr. 126, 380, 1996) to be an inhibitory effect on the activity of a fatty acid synthetase in a liver. In addition, each of a whole soybean globulin, a 7S globulin and a 11S globulin was examined for its effect on fats in blood and a liver, and was reported generally to be more excellent in terms of an ability of reducing blood cholesterol or neutral fat when compared with casein which is an animal protein (Okita et al., J. Nutr., 27, 379, 1981).

A 11S globulin-defect soybean, i.e., a 7S globulin-rich seed, which was obtained by a breeding, was also reported (Breeding Science, 46, 11, 1996) together with its utility (Breeding Science, 50, 101, 2000) and its patent (U.S. Pat. No. 6,171,640 B1).

Nevertheless, a soybean protein, including a 7S globulin, is known to form a complex with phytate by which the digestion of the soybean protein is affected adversely (M. A. Ritter, et al., J. Food Sci., 52, 325, 1987).

As soybean-derived proteins, proteins having high affinities with polar lipids as constituents of a cytoplasmic membrane as well as protein body or oil body membrane have also been identified and designated by Samoto et al. as "Oil-Body-Associated Proteins". An oil-body associated protein is a general term of the proteins consisting mainly of membrane proteins, especially those whose molecular weights measured by an SDS-polyacrylamide gel electrophoresis were 34 kDa, 24 kDa and 18 kDa, and exist as a fraction containing about 10 to 12% by weight of polar lipids which are extractable with a 2:1 polar solvent mixture of chloroform:ethanol, and were reported by Samoto et al. to be produced in an amount as high as about 35% of industrially produced fractionated soybean proteins (B.B.B., 62 (5), 935–940 (1998)). An oil-body-associated protein has a poor flavor and a high allergenicity.

Nevertheless, since an oil-body-associated protein is stained only slightly in an SDS-polyacrylamide gel electrophoresis employed frequently for determining the composition of a soybean protein, its estimated amount becomes far less than its actual amount or almost negligible. Thus, a conventional fractionation is focusing only on a 7S and an 11S, and pays no attention to the oil-body-associated proteins which are contaminating each fraction. However, from a physiological point of view, the behavior of these oil-body-associated proteins should be taken into account for the purpose of obtaining the 7S and the 11S at higher purities.

To prepare a 7S globulin efficiently from a soybean protein while cleaving phytate binding as a complex off and suppressing the contamination with the oil-body-associated proteins whereby raising the purity is very important in the use not only as an extremely safe pharmaceutical material for reducing the blood neutral fat but also as a food material.

OBJECTS OF THE INVENTION

An objective of the invention is to obtain a fraction having a blood neutral fat reducing ability from the soybean proteins and to treat this fraction for enhancing its ability, whereby providing it as a food or a pharmaceutical.

SUMMARY OF THE INVENTION

We studied intensively and obtained the following findings.

(1) When removing an 11S globulin by a method by Thahn and Shibasaki which is a standard procedure for fractionating the soybean proteins from a defatted soybean followed by fractionating a 7S globulin therefrom, a fractionation at a purity as high as 50% or higher is possible without using any reducing agent.

(2) When the 7S globulin described above and a 7S globulin obtained after cleaving phytate binding to the 7S globulin off (hereinafter referred to as a phytate-reduced 7S globulin) were subjected to a study in rats for 21 days using casein as a reference control, the 7S globulin and the phytate-reduced 7S globulin exhibited more excellent blood neutral fat reducing abilities when compared with the casein, with the phytate-reduced 7S globulin exhibiting an especially high neutral fat reducing effect.

(3) In response to the onset of this neutral fat reducing effect, the blood cholesterol level is reduced. While this cholesterol reducing ability is exhibited by both of the 7S globulin and the phytate-reduced 7S globulin, the HDL-cholesterol (HDLC) level is improved rather by the phytate-reduced 7S globulin.

The HDLC is so-called good cholesterol which recovers excessive cholesterols, and an improved HDLC leads to a great reduction in the arterial sclerosis index when combined with a total cholesterol reducing effect.

Arterial sclerosis index=(total cholesterol−HDL cholesterol)/HDL cholesterol (4) By further treating the soybean proteins with a phytate decomposing enzyme, a low phytin 7S globulin from which phytate has been cleaved off can be fractionated.

(5) By further removing a membrane protein rich oil-body-associated protein which contaminates a soybean protein, the efficacy of the 7S globulin as an active ingredient can further be enhanced.

As a result, it was discovered that by cleaving phytate off from a 7S globulin considered to have a blood neutral fat reducing effect and by removing oil-body-associated proteins to raise the purity a higher efficacy can be achieved together with a corresponding reduction in the dose, whereby establishing the present invention.

The invention provides a blood neutral fat reducing composition whose active ingredients are 7S globulin-rich phytate-reduced soybean proteins. Also provided is a blood neutral fat reducing composition whose active ingredient is a phytate-reduced highly purified 7S globulin which is a 7S globulin-rich soybean protein obtained by purifying a fraction containing a large amount of a 7S globulin as a major constituent of the soybean proteins to a protein purity (on the basis of SPE described below) as high as 50% or higher, in which the chloroform:methanol-extractable polar lipids as the indexes of the oil-body-associated protein have been reduced to a level of ⅓ or less and in which the phytate content, which is about 2% based on the proteins in a commercial soybean protein product, has been reduced to a level of 0.2% or less based on the proteins by cleaving phytate off. Thus, by means of a fractionation involving a suppression of the contamination with the membrane protein rich oil-body-associated proteins as far as possible and a cleavage of phytate, a blood neutral fat reducing composition having a further enhanced efficacy can be provided. On the other hand, by employing a phytate decomposing enzyme during the manufacturing process of a soybean protein, the fractionation of a 7S globulin is facilitated, whereby providing a blood neutral fat reducing composition containing as an active ingredient a highly purified phytate-reduced 7S globulin resulting from a reduction in phytate to 0.2% or less based on the proteins and from a reduction in the oil-body-associated proteins to 10% or less. Also provided is a blood neutral fat reducing composition produced without using any reducing agents during the manufacturing process described above.

DETAILED DESCRIPTION OF THE PREFERRED EMBODIMENTS

In this invention, a 7S globulin means a globulin whose ultracentrifugation sedimentation coefficient is 7S among the soluble globular proteins referred to generally as globulins. Based on the molecular weight distribution, the globulins are classified into 2S, 7S, 11S and 15S, among which 7S and 11S are known to be abundant in the depot proteins of a pulse plant such as a soybean. The 7S globulin of a soybean is substantially the same to β-conglycinin which is an immunological term.

In this invention, a 7S globulin-rich fraction obtained from soybean proteins is employed as a main ingredient. The first step for fractionating the 7S globulin from the soybean proteins involves a removal of an 11S globulin. This removal can be effected by a method by Thahn and Shibasaki (Thahn, V. H., and Shibasaki, K., J.Agric.Food Chem., 24, 117, 1976) which is employed widely in these days for obtaining each globulin fraction, as well as a cold insoluble fraction (CIF) method utilizing a cryoprecipitation (Briggs, D. R., and Mann, R. L., Cereal Chem, 27, 243, 1950) and a fractionation with adding 0.1 N calcium chloride proposed by Wolf et al (Wolf, W. J., and Sly, D. A., Cereal Chem, 44, 653, 1967). A fraction made free of the 11S and the oil-body-associated proteins by the method described below in Production example 2 may also be employed.

After removing the 11S globulin by any of the methods described above, a 7S globulin is fractionated by an ordinary method for preparing an isolated soybean protein. In such procedure, a 7S globulin having a purity which is sufficiently acceptable for use can be obtained in the absence of a reducing agent, and such absence of the reducing agent is favorable for a wider application also when being used as a neutral fat reducing agent. A 7S globulin-rich soybean protein whose protein purity (on the basis of SPE) is 50% or higher, preferably 60% or higher, more preferably 80% or higher, particularly 85% or higher can be obtained. The 7S globulin-rich fraction thus obtained is further subjected to a treatment with an enzyme having a phytate decomposing activity such as phytase or phosphatase or a formulation thereof, whereby cleaving phytate off. As a result, the blood neutral fat reducing ability possessed naturally by a phytate-reduced 7S globulin obtained by cleaving phytate to a level of 0.2% or less, preferably 0.1% or less, more preferably 0.05% or less based on the proteins is enhanced.

A method for fractionating the phytate-reduced 7S globulin obtained by cleaving phytate as described above may be accomplished simultaneously with a removal of a 11S globulin by treating a soybean protein directly with an enzyme having a phytate decomposing activity such as phytase and phosphatase as well as a formulation thereof.

Further by removing the oil-body-associated proteins, the blood neutral fat reducing ability of the phytate-reduced 7S globulin can further by enhanced. For this purpose, the oil-body-associated proteins can be removed as a precipitation at pH 5.6 to 6.8 after heating (30 to 75° C.) at a weakly acidic pH (pH 3.8 to 6.8) at which they tend to be insoluble.

A composition of the invention can be formulated as an oral composition whose active ingredient is a fraction obtained as described above or a soybean protein, and formulated into various dosage forms such as powders, sugar-coated tablets and granules by known methods optionally together with other excipients and additives.

A fraction or a soybean protein employed as an active ingredient according to the invention is a safe edible material the amount of which to be incorporated into a composition or to be ingested is not limited particularly, and may be ingested as it is or may be incorporated into a food product for a dietary therapy. A preferable amount to be ingested per kg body weight is 50 to 500 mg, preferably 100 to 300 mg as 7S globulin-rich phytate-reduced soybean proteins.

EXAMPLES

The usefulness of the present invention is further discussed in the following examples, which are not intended to restrict the technical spirit of the invention.

Major analytical methods employed in the invention are described below.

Crude protein; Based on a Kjeldahl method, a nitrogen content was determined and multiplied by the coefficient 6.25 to convert into a crude protein.

SDS-Polyacrylamide electrophoresis; Based on a method by Laemmli (Nature, 227, 680 (1970)), an analysis was conducted with a gradient gel concentration from 10 to 20%. The amount of a sample applied was 10 μg.

Phytate; A method by Alii Mohamed (Cereal Chemistry 63, 475–478, 1986) was employed.

Chloroform methanol-extractable oil fraction; A dried sample was combined with an about 50-fold volume of a mixture of chloroform and methanol (2:1, v/v) and the weight ratio of the solids extracted by reflux was determined as a chloroform methanol-extractable oil portion.

Purity (SPE standard); The pattern of the bands obtained in the SDS-polyacrylamide electrophoresis described above was measured by a densitometer and a % area of the corresponding band based on the total area was represented as a purity (on basis of SPE). A 7S globulin content mentioned here means the total amount of α, α' and β subunits, while an 11S globulin content means the total amount of acidic polypeptides (A) and basic polypeptides (B).

Corrected purity; Based on a purity (on basis of SPE) obtained above and taking any contaminating oil-body-associated proteins, a corrected purity was calculated as described below. Thus, a purity of a sample (on basis of SPE) is represented as A %, and a purity is calculated as a value based on the total proteins including the 7S globulin, the 11S globulins and the oil-body-associated proteins, since the sample contains the oil-body-associated proteins in an amount at least 10 times the chloroform-methanol-extractable oil portion in addition to the 7S globulin and the 11 S globulin.

Corrected purity (%)=(100 (%)−chloroform·methanol-extractable oil portion (%)*10)*A (%)/100

Neutral fats, total cholesterols, HLD cholesterols (HDLC); A DRYCHEM model 5500 manufactured by FUJI FILM was employed in a solid phase method.

Preferred embodiments of the invention are described below.

Production Example 1

Preparation of 7S Globulin="7S" and Phytate-Reduced 7S Globulin="7S-PH")

A defatted soybean was combined with water at a weight ratio of 1:10 and stirred with adjusting at pH 7.0 for 1 hour and then centrifuged (4000 r.p.m, 20° C., 10 minutes) to remove a precipitate. The resultant supernatant was adjusted at pH 6.4, allowed to stand at 4° C. overnight and centrifuged (4000 rpm, 4° C., 10 minutes) to remove the precipitate. The resultant supernatant was adjusted at pH 4.5 and centrifuged (4000 rpm, 4° C., 10 minutes), and the resultant precipitate was recovered as a 7S globulin curd.

This 7S globulin curd was combined with a 4-fold volume of water, adjusted at pH 6.0, supplemented with phytase (NOVO, PHYTASE NOVO L) at 0.2% based on the proteins, and then allowed to react at 40° C. for 1 hour. The reaction mixture was adjusted at pH 5.0, centrifuged (4000 r.p.m., 20° C., 10 minutes) to remove a whey fraction, whereby obtaining a phytate-reduced 7S globulin curd. The both of the 7S globulin curd and the phytate-reduced 7S globulin curd were hydrated and then neutralized at pH 7.0, sterilized at 140° C. for 15 seconds, and then rapidly spray-dried to obtain a 7S globulin and a phytate-reduced 7S globulin. Each of the 7S globulin and the phytate-reduced 7S globulin thus obtained was subjected to a SDS-polyacrylamide gel electrophoresis, and the intensity of the color of a stained protein band revealed that the purity was 80%. The phytate contents in the both were 1.8% and 0.05%, respectively, revealing that the phytase treatment resulted in an almost complete cleavage of the phytate. The chloroform methanol-extractable oil portion of this sample was 2.8%. On the other hand, the total amount of the sulfur-containing amino acids cystine and methionine was 25 mg/g protein, which was higher than 5 mg/g protein exhibited naturally by a purified 7S, suggesting that a substantial amount of impurities still remained.

Production Example 2

Preparation of Highly Purified Phytate-Reduced 7S Globulin:"7S-PH-LP")

One part by weight of a low-modified defatted soybean was combined with 10 parts by weight of extraction water at 40° C., and adjusted at pH 5.3 with hydrochloric acid. This solution was supplemented with 8 units per protein of phytase (NOVO, PHYTASE NOVO L) and subjected to a protein extraction simultaneously with an enzyme reaction for 30 minutes at 40° C. to obtain an enzyme-treated slurry extract. This enzyme-treated slurry extract was cooled to about 25° C., adjusted at pH 6.1 with hydrochloric acid, and centrifuged (3000G) using a batch-type centrifuge. Upon this, a discrete separation between a soluble fraction and an insoluble fraction was observed. The solution temperature of this centrifuge was about 25° C. Subsequently, the soluble fraction was adjusted at pH 4.9 with hydrochloric acid, and centrifuged to obtain a precipitate curd. The precipitate curd was washed with a 10-fold volume of water, hydrated (to 4-fold weight), neutralized with sodium hydroxide, sterilized at 140° C. for 15 seconds, and then rapidly spray-dried to obtain a phytase-treated 7S globulin-rich fractionated soybean protein ("7S-PH-LP").

The phytate-reduced 7S globulin thus obtained was subjected to an SDS-polyacrylamide gel electrophoresis and the intensity of the color of a stained protein band revealed that the purity was 95%. The phytate content was 0.05% based on the proteins, indicating almost complete cleavage of the phytate. On the other hand, the chloroform.methanol-extractable oil portion of this sample was 0.5%, which was substantially lower when compared with production example 1. The total amount of the sulfur-containing amino acids cystine and methionine was 12 mg/g protein, suggesting that a highly purified 7S was obtained whose impurities were substantially low in view of the value 5 mg/g protein exhibited naturally by a purified 7S.

Example 1

Verification of Blood Neutral Fat Reducing Effect in Rats

A blood neutral fat reducing effect was verified in rats. Each feed employed here contained as a dietary protein the soybean protein obtained in production example 2 described above or casein (vitamin-free casein, ORIENTAL YEAST) as a control at the concentration of 20%, together with 0.5% of cholesterol and 0.125% of sodium cholate as well as a 1:2 mixture of sucrose and corn starch. A typical formulation is represented in table 1 shown below.

TABLE 1

Feed formulation of each treatment group

| Component | Composition (%) |
|---|---|
| Protein | Adjusted at 20% as crude protein with α-corn starch |
| Sucrose | 20.0 |
| Corn oil | 5.0 |
| Vitamin mix | 1.0 |
| Mineral mix | 3.5 |
| Powdered cellulose | 5.0 |
| Choline hydrogen tartarate | 0.2 |
| Cholesterol | 0.5 |
| Sodium cholate | 0.125 |
| α-Corn starch | to 100 in total |

Experimental animals were 5-week old (growing period) and 20-week old (mature period) male Wistar rats (weighing from 100 to 120 g, and 330 to 360 g) purchased from NIPPON SLC, and received a commercial solid chow (ORIENTAL YEAST, CRF-1) preliminarily for 1 week, and then divided into two treatment groups in total each consisting of 6 animals with no deviation in the body weight between groups, and the animals were raised for 10 days with test feeds. Each rat was housed in an individual cage at a temperature of 23±1° C. and a humidity of 55±5% under a 12-hour lighting period (7:00 am to 7:00 pm). During the raising period, the animals were allowed to receive water and feed ad libitum.

The treatment period was 10 days, during which the body weight was monitored. The results are represented in tables 2 and 3 shown below. No significant difference in the weight gain was observed between the groups.

TABLE 2

Change in body weight in treatment group of 5-week old rats, unit: g

| Treatment group | Casein | Phytate-reduced 7S globulin (7S-PH) |
|---|---|---|
| Initiation of treatment | 153.3 ± 1.3 | 153.3 ± 1.3 |
| Termination of treatment | 201.7 ± 1.3 | 192.0 ± 1.5 |
| Weight gain | 48.4 ± 1.3 | 38.7 ± 1.6 |

TABLE 3

Change in body weight in treatment group of 20-week old rats, unit: g

| Treatment group | Casein | Phytate-reduced 7S globulin (7S-PH) |
|---|---|---|
| Initiation of treatment | 357.2 ± 2.7 | 356.4 ± 5.8 |
| Termination of treatment | 358.7 ± 3.7 | 352.0 ± 10.3 |
| Weight gain | 0.3 ± 2.1 | 4.4 ± 4.6 |

After the 10-day treatment period, each animal was fasted for 7 hours from the morning (8:00 am) on the 11th day, and then subjected to a laparotomy under an anesthesia with nembual, and a blood was taken from an abdominal aorta via a heparinized syringe. The blood was centrifuged (3000 r.p.m., 5° C. for 15 minutes) to separate a plasma, which was examined for the neutral fats and the cholesterols. The mean and the standard deviation of the data in each group were calculated, and a statistical significance was analyzed using Duncan's multiple range test. The results are shown in tables 4 and 5. In the tables, a % neutral fat reduction and a % cholesterol reduction are the ratios (%) of the difference in respective data between the casein group and the treatment group based on the data in the casein group.

TABLE 4

Change in blood neutral fats in treatment group of 5-week old rats

| Treatment group | Casein | Phytate-reduced 7S globulin (7S-PH) |
|---|---|---|
| Neutral fat level | 176.2 ± 10.9 | 89.1 ± 5.7 |
| % Neutral fat reduction | — | 49.6 |
| Total cholesterol level | 144.1 ± 6.0 | 93.5 ± 2.9 |
| % Cholesterol reduction | — | 35.1 |

Unit; (Level) mg/dl, (ratio) %

TABLE 5

Change in blood neutral fats in treatment group of 20-week old rats

| Treatment group | Casein | Phytate-reduced 7S globulin (7S-PH) |
|---|---|---|
| Neutral fat level | 261.2 ± 22.5 | 108.6 ± 21.6 |
| % Neutral fat reduction | — | 58.4 |
| Total cholesterol level | 132.5 ± 3.5 | 92.8 ± 14.5 |
| % Cholesterol reduction | — | 30.0 |

Unit; (Level) mg/dl, (ratio) %

As evident from the data shown above, the phytate-reduced 7S globulin exhibited marked cholesterol- and blood neutral fat-reducing effects in both of the growing period (5-week old) and the mature period (20-week old).

Comparative Example 1

Verification of Blood Neutral Fat Reducing Effect in Rats

Similarly to example 1, a blood neutral fat reducing effect was verified in rats. A treatment chow had the composition similar to that in example 1, except for using as a soybean protein the 7S globulin (7S) obtained in production example 1.

Experimental animals were 5-week old male Wistar rats (weighing from 90 to 10 g) purchased from NIPPON SLC, and received a commercial solid chow (ORIENTAL YEAST, CRF-1) preliminarily for 1 week, and then divided into two treatment groups in total each consisting of 6 animals with no deviation in the body weight between groups, and the animals were raised for 3 weeks with test feeds. Each rat was housed in an individual cage at a temperature of 23±1° C. and a humidity of 55±5% under a 12-hour lighting period (7:00 am to 7:00 pm). During the raising period, the animals were allowed to receive water and feed ad libitum.

The treatment period was 21 days, during which the body weight was monitored. The results are represented in table 6 shown below. No significant difference in the weight gain was observed between the groups.

TABLE 6

Change in weight in treatment group Unit: g

| Treatment group | Casein | 7 globulin (7S-PH) |
|---|---|---|
| Initiation of treatment | 151.0 ± 1.3 | 151.1 ± 0.9 |
| Termination of treatment | 243.8 ± 1.6 | 240.8 ± 5.5 |
| Weight gain | 92.7 ± 1.5 | 89.7 ± 6.0 |

After the 21-day treatment period, each animal was fasted for 6 hours from the morning (8:00 am) on the 22nd day, and then subjected to a laparotomy under an anesthesia with nembual, and a blood was taken from an abdominal aorta via a heparinized syringe. The blood was centrifuged (3000 r.p.m., 5° C. for 10 minutes) to separate a plasma, which was examined for the neutral fats and the cholesterols. The mean and the standard deviation of the data in each group were calculated, and a statistical significance was analyzed using Duncan's multiple range test. The results are shown in table 7. Each % reduction was determined by a method similar to those for tables 4 and 5 in example 1.

TABLE 7

Change in blood neutral fats in treatment group Unit: g

| Treatment group | Casein | 7S globulin (7S-PH) |
|---|---|---|
| Neutral fat level | 190.4 ± 12.2 | 122.7 ± 6.6 |
| % Neutral red reduction | — | 35.6 |
| Total cholesterol level | 118.7 ± 4.5 | 109.9 ± 5.8 |
| % Cholesterol reduction | — | 7.4 |

Unit; (Level) mg/dl, (ratio) %

When compared with the cholesterol- and neutral fat-reducing effects of the phytate-reduced 7S globulin employed in example 1 relative to casein, the reducing effect of the 7S globulin in comparative example 1 was lower, revealing that the phytate-reduced 7S globulin had a higher blood fat improving effect when compared with the 7S globulin.

Example 2

The blood neutral fat reducing effect of the highly purified phytate-reduced 7S globulin (7S-PH-LP) prepared in production example 2 was investigated. As controls, the casein employed in example 1, the 7S globulin (7S), the phytate-reduced 7S globulin (7S-PH) and a commercial separated soybean protein (SPI) were employed. The composition of each protein is shown in table 8.

TABLE 8

| | Unit: % | | | |
|---|---|---|---|---|
| | SPI | 7S | 7S-PH | 7S-PH-LP |
| Crude protein | 86.2 | 88.0 | 90.5 | 92.3 |
| Purity (on basis of SPE) | — | 80.0 | 82.2 | 95.7 |
| Chloroform · methanol-extractable oil fraction | 3.2 | 2.8 | 2.8 | 0.5 |
| Phytate | 1.8 | 1.8 | 0.05 | 0.05 |
| Corrected purity | — | 57.6 | 59.2 | 90.9 |

5-Week old rats similar to those in example 1 were employed as experimental animals and raised for 2 weeks during which the body weight was monitored under the conditions similar to those in example 1. After the treatment period, a blood was taken similarly to example 1, and examined for the neutral fats and the cholesterols.

The results included the change in the body weight shown in table 9, and the neutral fats, the cholesterol, HDLC and the arterial sclerosis index calculated therefrom shown in table 10.

TABLE 9

| | Unit: g | | | | |
|---|---|---|---|---|---|
| | Casein | SPI | 7S | 7S-PH | 7S-PH-LP |
| Initiation of treatment | 138.5 | 138.7 | 135.8 | 135.5 | 137.8 |
| Termination of treatment | 210.2 | 212.9 | 206.9 | 179.6 | 206.5 |
| Weight gain | 71.7 | 74.3 | 71.1 | 44.0 | 68.8 |

TABLE 10

| | Unit; mg/dl | | | | |
|---|---|---|---|---|---|
| | Casein | SPI | 7S | 7S-PH | 7S-PH-LP |
| Neutral fat level | 178.3 | 120.0 | 105.0 | 92.7 | 91.0 |

TABLE 10-continued

| | Unit; mg/dl | | | | |
|---|---|---|---|---|---|
| | Casein | SPI | 7S | 7S-PH | 7S-PH-LP |
| Total cholesterol level | 125.6 | 88.3 | 88.3 | 90.8 | 87.3 |
| HDLC | 37.1 | 36.8 | 34.2 | 43.5 | 44.0 |
| Arterial sclerosis index | 2.39 | 1.40 | 1.58 | 1.09 | 0.98 |

Based on the results described above, the neutral fat- and the cholesterol-reducing effects were higher in the order shown below, Casein<<SPI=7S<7S-PH<7S-PH-LP and HDLC was revealed to be improved in a phytate-free group. Thus, the highly purified phytate-reduced 7S globulin obtained by removing phytate and also by removing the oil-body-associated proteins exhibited the most evident serum lipid improving effect, especially an arterial sclerosis index reducing effect.

INDUSTRIAL APPLICABILITY

The present invention enables an efficient reduction in the blood neutral fat level, and an inventive composition, which is highly safe, is not only useful as a prophylactic or therapeutic agent for the purpose of reducing the blood neutral fat level but also capable of serving as a food product for such purpose.

What is claimed is:

1. A composition for reducing the blood level of neutral fats, comprising as an active ingredient a 7S globulin-rich phytate-reduced soybean protein, whose phytate content is 0.2% or less based on the soybean protein, wherein the composition is capable of reducing the blood level of neutral fats.

2. The composition according to claim 1 comprising 10% or less of an oil-body-associated protein based on the soybean protein.

3. The composition according to claim 1 comprising 1% or less of a chloroform:methanol (2:1)-extractable oil portion base on the soybean protein.

4. The composition according to claim 1 which is obtained by reacting a soybean protein with a phytate decomposing enzyme.

5. The composition according to claim 1 which is prepared without using any reducing agents over its manufacturing process.

6. A method of reducing the blood level of neutral fats, comprising administering the composition of claim 1 to a subject in need of reducing the blood level of neutral fats.

* * * * *